(12) United States Patent
Vermeulen et al.

(10) Patent No.: US 7,247,309 B2
(45) Date of Patent: Jul. 24, 2007

(54) COCCIDIOSIS VACCINES

(75) Inventors: Arnoldus Nicolaas Vermeulen, Korhoederveld (NL); Theodorus Petrus Maria Schetters, Sering (NL)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 09/739,561

(22) Filed: Dec. 18, 2000

(65) Prior Publication Data
US 2001/0005910 A1    Jun. 28, 2001

(30) Foreign Application Priority Data
Dec. 21, 1999  (EP) ................... 99204444

(51) Int. Cl.
*A61K 39/012* (2006.01)
*A61K 39/00* (2006.01)
*A61K 39/116* (2006.01)
*A61K 39/12* (2006.01)

(52) U.S. Cl. ............... 424/267.1; 424/184.1; 424/203.1; 424/204.1; 424/271.1

(58) Field of Classification Search ............ 424/184.1, 424/203.1, 204.1, 267.1, 271.1, 20.1, 271; 435/243, 252.1, 258.4, 252, 41, 258.1
See application file for complete search history.

(56) References Cited

FOREIGN PATENT DOCUMENTS

| EP | 0-047662 | * | 2/1982 |
| EP | 0 047 662 | | 3/1982 |
| EP | 0 256 878 | | 2/1988 |
| EP | 0 506 211 | | 9/1992 |
| WO | WO 94/16725 | * | 8/1994 |

OTHER PUBLICATIONS

Peeter et al, (Avian Diseases 38:483-493, 1994).*
Stephan et al, Veterinary Parasitology 69:19-29, 1997.*
Peeters et al, Avian Diseases, 38:483-493, 1994.*
Williams, International Journal of Parasitol, 1998, 28(7), p. 1089-1098.*
Kim et al, Infection and Immunity, Aug. 1989, p. 2434-2440.*
Peeters et al, (Avian Diseases 38:483-493, 1994).*
Han Qian et al., "A Survey of drug resistance to coccidiosis of Eimeria spp. Isolated from Liaocheng, Shandong Province in China" Acta Parasitologica et Medica Entomologica Sinica (1999) vol. 6, No. 2, p. 84-88 (Abstract).
Liu Qun et al., "Coccidiostats resistance of Eimeria spp. Isolates from Weifang, Shandong Province in China" Acta Veterinaria et Zootechnica Sinica, (1999) vol. 30, No. 2, p. 187-192 (Abstract).
Han Qian et al., "Survey of the coccidiostats resistance of Eimeria isolates from Zhucheng, Shandong Province in China" Chinese Journal of Veterinary Science, (1999) vol. 19, No. 1, p. 40-42 (Abstract).
Salisch et al., "Efficacy of Diclazuril and Four Ionophorous Anticoccidials Against Eimeria-Tenella and Eimeria -Acervulina" Archiv Fuer Gefleuglekunde, vol. 53, No. 3, 1989, p. 111-115 (Abstract).
Peeters et al., "Sensitivity of avian Eimeria spp. To seven chemical and five ionophore anticoccidials in five Belgian integrated broiler operations." Avian Diseases, vol. 38, No. 3, (1994) p. 483-493 (Abstract).
Stephan et al., "Studies of resistance of anticoccidials in Eimeria field isolates and pure Eimeria strains." Veterinary Parasitology, vol. 69, No. 1-2, 1997, p. 19-29 (Abstract).

* cited by examiner

*Primary Examiner*—Jeffrey Siew
*Assistant Examiner*—Vanessa L. Ford
(74) *Attorney, Agent, or Firm*—TraskBritt (57) ABSTRACT

The present invention relates to coccidia strains and, in one embodiment, to microbiological cultures comprising such strains. In preferred embodiments, the coccidia strains are selected for tolerance to one group of coccidiostatic drugs, sensitivity to a second group of coccidiostatic drugs, and decreased proliferative capacity. Another embodiment of the invention relates to vaccines based on the coccidia strains according to the invention.

4 Claims, 2 Drawing Sheets

Figure 1. Relative tolerance of strains according to the invention, to ionophores. Data represent the reduction in oocyst output as compared to that of unmedicated controls. The strains are fully sensitive to a non-ionophore anticoccidial (diclazuril).

COCCIDIOSIS VACCINES

BACKGROUND OF THE INVENTION

1. Field of the Invention

The present invention relates to coccidiosis strains, microbiological cultures comprising such strains, vaccines based thereon, use of such strains for the preparation of such vaccines and methods for the preparation of such vaccines.

2. State of the Art

Coccidiosis is a highly contagious disease that has been known for a long time. Coccidiosis is known to occur in many economically important animal species, such as chickens, cattle, sheep, rabbits, goats, and turkeys. The causative agent of this disease is a parasite of the genus *Eimeria*. This parasite is a member of the coccidia. Poultry coccidiosis, in particular, is a problem world wide. High stocking densities and specific housing conditions in the modern poultry industry facilitate the spread of coccidia, as there is little or no separation between animals and fecal matter. Since the oocysts are extremely resistant, surviving even partial desiccation, bleaching, and chemical treatment with most disinfectants, it is extremely difficult to avoid environmental contamination with oocysts.

The parasites cause an enteritis in the gut in general, more specifically in poultry. The infection severely attacks the epithelium of the intestines. Therefore, the first clinical signs of infection with the parasite are, e.g., diarrhea. Later in infection, a broader scale of clinical signs becomes manifest, including reduced food intake, malabsorption, decrease in feed conversion efficiency, and reduced weight gain. In the worst case, the infection is lethal. Gregory M W "Pathology of coccidial infections," *Coccidiosis of man and domestic animals* (Ed.: P. L. Long) CRC Press, Boca Raton, Fla. Pp. 235-261 (1990); Ruff M D "Pathophysiology and coccidial infections," *Coccidiosis of man and domestic animals* (Ed.: P. L. Long) CRC Press, Boca Raton, Fla. Pp. 263-280(1990). Even when the infection develops non-lethally and the animal recovers, the economic losses due to reduced weight gain are large world wide, especially in the many countries where poultry is an important food source. Costs involved in controlling the disease are estimated to exceed USD $600,000,000 yearly.

Apart from factors such as housing conditions, general state of health, age, immune status and genetic make-up of the host, the degree of pathogenicity depends primarily on the *Eimeria* species. Ruff, M. D., *Proceedings of the VI$^{th}$ International Coccidiosis Conference* (Eds.: J. R. Barta and M. A. Fernando) Moffit Print Craft Ltd., Guelph. Pp. 73-79 (1993). The genus *Eimeria* comprises at least seven named species: *E. tenella, E. necatrix, E. maxima, E. brunetti, E. acervulina, E. mitis* and *E. praecox*. Of these, *E. tenella* and *E. necatrix* are the most pathogenic, followed by *maxima* and *brunetti*. Rose, M. E. and Long, P. L. "Vaccination against coccidiosis in chickens." Vaccines against parasites (Eds.: A. E. R. Taylor, and R. Muller) Blackwell Scientific Publication, Ltd., Oxford, U.K. pp. 57-74 (1980). Infection with *E. tenella* and *E. necatrix* leads to hemorrhage and, in heavy infections, to anemia and death due to blood loss and shock.

Currently, two ways of controlling coccidiosis in chicken are available: chemical treatment with anticoccidial drugs and vaccination. Treatment with anticoccidial drugs has two important advantages: (1) it can be started directly after birth of the animal, and (2) it is cost-effective. There are also two important disadvantages: (1) an increasing level of resistance against various anticoccidial drugs is seen, and (2) there is an increasing reluctance towards the use of drugs from the point of concern about public safety.

Vaccination also offers a means of protecting against coccidial infection. Vaccination by mixing carefully determined small amounts of fully virulent strains with feed or drinking water is well known in the art. This method of vaccination is efficient but has some serious drawbacks: (1) the amount of oocysts given must be determined very carefully, and (2) animals that did not eat/drink enough at the day of vaccination become severely infected later on by the enormous amount of progeny oocysts that are produced when the vaccine strain recycles through the flock.

Vaccination with attenuated vaccines is also used in the art but only on a very modest scale. Such vaccines are highly amenable to reversion to virulence. Also, as a result of their attenuation, they suffer from severe loss of immunogenicity so that high numbers of oocysts must be given. Production thereof is, however, difficult and less cost-effective. Vaccination with subunit vaccines has not been shown to be sufficiently efficient so far.

Additionally, each vaccination unavoidably has the disadvantage that it takes at least 14-21 days before immunity builds up. Therefore, there is always a serious risk of infection in the days before the vaccination gives protection. And in practice, given the high infection pressure, this risk is too large to be taken.

Summarizing what is said about chemical treatment and vaccination, both can work but have their specific disadvantages. A combined treatment with both coccidiostatic drugs and vaccines comprises feeding coccidiostatic drugs the first few days combined with vaccination at the day of hatching seems attractive because the coccidiostatic drugs then only have to be used until immunity through vaccination has built up. This approach, however, is not easily feasible because the presence of the coccidiostatic drug kills not only infecting oocysts from the field but also the vaccine strains used to build up immunity.

A possible way out of this dilemma has been proposed in the Dutch Patent Application NL 8802399. In this application it was suggested to start as soon as possible with treatment with coccidiostatic drugs, followed by vaccination with specific *Eimeria* strains that are resistant against the coccidiostatic drug being administered.

Even these strains suffer, however, from drawbacks:

the strains used are not attenuated, therefore they are potentially dangerous; and once introduced in the poultry industry, it is very difficult to remove these strains.

This is a serious problem since the strains are virulent and resistant at the same time. Large amounts thereof, as shedded after recycling through the flock, can easily infect subsequent groups of young birds kept in the same housing.

BRIEF SUMMARY OF THE INVENTION

It is an object of the present invention to provide *Eimeria* strains that do not suffer from the disadvantages of the strains mentioned above and that are, thus, very suitable for combined use with specific coccidiostatic drugs.

The strains according to the invention have the following characteristics:

they are tolerant for at least one group of coccidiostatic drugs;

they are sensitive to at least one other group of coccidiostatic drugs; and they show a decreased proliferative capacity (dpc).

This makes them very suitable for use in vaccines for a combined anticoccidial approach: they can be combined from the beginning with coccidiostatic drugs for which they are tolerant, their proliferation number is relatively low, and, if necessary, they can be completely removed from the animals after the therapy.

Therefore, one embodiment of the present invention relates to *Eimeria* strains that are tolerant for a first group of coccidiostatic drugs, sensitive to a second group of coccidiostatic drugs, and have a decreased proliferative capacity.

BRIEF DESCRIPTION OF THE DRAWINGS

all four strains are tolerant to two commonly used anticoccidial ionophores: monensin (110 ppm) and salinomycin (60 ppm). The concentrations tested are commonly used concentrations. Specific tolerance levels were determined by infection of chickens with the strains and administration of ionophores.

all four strains are fully sensitive to the non-ionophore anticoccidial drug diclazuril (1 ppm).

DETAILED DESCRIPTION OF THE INVENTION

Different groups of coccidiostatic drugs are considered to be groups that have a different mode of action. A first and rough division can be made by dividing the coccidiostatic drugs on the basis of their action in three main groups: 1) the group of drugs that are involved in inhibition of DNA synthesis, 2) the group involved in inhibition of protein synthesis, and 3) the group involved in destruction of membrane integrity, such as, e.g., the ionophoric drugs.

Drugs of the first group are, e.g., decoquinate, clopidol, arprinocid, amprolium, letrazuril, toltrazuril, and diclazuril. Drugs of the second group are, e.g., clindamycin, spiramycin and clarithromycin. Drugs of the third group are, e.g., monensin, salinomycin, narasin and maduramicin. Haberkorn A, *Parasitology Research* 82: 193-199 (1996), Wang, C C, *Parasitology* 114: 31-44 (1997), Croft, S L, *Parasitology* 114: 3-15 (1997), Proceedings of the Bayer workshop "Diseases related to protozoa and possibilities for treatment" at the 17$^{th}$ International Conference of the WAAVP, Aug. 15-19, 1999; Greif, G. et al., *Chemotherapeutic approaches to protozoa*, p. 32-33.

It must be mentioned here that coccidiostatic drugs within one group may differ quite considerably in their mode of action. The following may serve as an example: arprinocid and amprolium both belong to the group of coccidiostatic drugs interfering with DNA synthesis and, thus, they both belong to one group, but they clearly differ in their mode of action. Arprinocid belongs to a subgroup that inhibits hypoxanthine and guanine uptake into infected eukaryotic cells, whereas amprolium belongs to a subgroup that competitively inhibits thiamin transport across the cell membranes of 2nd generation schizonts. It is, therefore, possible to select for coccidia that are tolerant for arprinocid but sensitive to amprolium.

Therefore, it is equally possible to select coccidia with a specific tolerance for one drug of, e.g., group one having a specific mode of action, without interfering with the sensitivity for another drug of that same group having another mode of action. Therefore, the meaning of "group" in the definition given above applies equally well to groups as defined above as to subgroups within each group that have a distinct mode of action.

Strains according to the invention can be obtained, e.g., through tolerance selection with a coccidiostatic drug of one group followed by selection for decreased proliferative capacity (dpc). Sensitivity for coccidiostatic drugs of other groups can in principle be safely assumed but can be tested if desired.

Methods for the selection of resistance to coccidiostatic drugs have been described in the literature. For monensin, e.g., it has been described by Chapman, *Parasitology* 89: 9-16(1984) and Zhu et al. *Veterinary Pathology* 51:211-217 (1994).

Such selection, regardless the group of coccidiostatics to which tolerance is desired, is done quickly as follows. Ten coccidiosis free chickens receive a low sub-lethal dose of a coccidiostatic drug on a daily basis through their drinking water or feed. A suitable low sub-lethal dose would be a dose that is about 10% of the minimal lethal dose. At some moment in time, they are infected with, e.g., $10^3$-$10^6$ oocysts. At 5-9 days after infection, or possibly later if the cycle is not yet completed at day 9, the shedded oocysts are recovered from the droppings by standard methods. About $10^3$-$10^6$ of these oocysts are administered to 10 chickens that receive 25% of the minimal lethal dose of the coccidiostatic drug. The procedure is then repeated in chickens receiving 40, 60, 80, and 100% of the minimal lethal dose of the coccidiostatic drug. Coccidia recovered from these chickens are tolerant and fulfill the first requirement of strains according to the invention.

The following figures may serve merely as an example: for the selection of monensin-tolerant coccidia, such selection can advantageously be done using $10^4$-$10^5$ coccidia, recovering shedded oocysts after 5-9 days, and giving 50, 75, 100, and 125 ppm monensin, respectively. For the selection of salinomycin, the same approach can be used but with amounts of 10, 20, 30, 40, 50, and 60 ppm.

Of the coccidia recovered after this first procedure, 10 sporulated oocysts are randomly selected and passed through one coccidiosis free chicken each. Selection of individual oocysts is easily done by microscopical techniques. From each of these chickens, the droppings from day 5-9 are collected, and the number of shedded oocysts is determined. This can easily be done by standard procedures well known in the art. From the chicken that shedded the lowest number of oocysts, 10 randomly selected oocysts are used to infect 10 coccidiosis free chickens. This procedure is repeated if a first selection does not give the degree of dpc that is required. The resulting oocysts will have as inherent characteristics both a decreased proliferative capacity and tolerance against certain coccidiostatic drugs.

A decreased proliferative capacity is defined as follows: if, e.g., 100 coccidia of a certain type are administered to a chicken, this chicken sheds, depending on the type of coccidia, typically a million times as many coccidia, e.g., $10^8$ coccidia. A strain of that same type of coccidia that is selected for its decreased proliferative capacity would under the same conditions, shed about 8×10⁷ coccidia, or even much less than that. In other words, a coccidial strain that after one cycle produces 80% or less of the number of oocysts that the wild-type strain produces is considered to have a decreased proliferative capacity. A dpc that is between 1 and 50% of the wild-type proliferative capacity is preferred. Within this range, a dpc between 5 and 10% is more preferred.

Finally, a certain percentage of the resulting population is passed through chickens treated with another coccidiostatic drug of a group for which no selection has been applied. In principle, since no selection for this other group was applied, no tolerance for this group can be expected. Nevertheless, for safety reasons, this check can be performed. If, as expected, no survivors are found, the population as a whole has all the characterizing features of the strains according to the invention.

The methods given above are equally applicable to all *Eimeria* strains, regardless the species. They work for, e.g., *E. tenella* as well as for, e.g., *E. maxima* or *E. necatrix*.

A tolerant strain is considered to be a strain of which a certain percentage of the oocysts administered survives the presence of a standard amount of a coccidiostatic drug. A full tolerance, i.e. 100% tolerance, would be the most preferred situation. Percentages of between 10-100% tolerance are very suitable percentages. Percentages of between 20-100% tolerance are a preferred range.

Nevertheless, even strains that are between 1 and 10% tolerant against a coccidiostatic drug can be used for inducing immunity. Giving more coccidia per vaccination can easily make up for the lower amount of coccidia surviving the coccidiostatic drug treatment. Percentages of below 1% tolerance of the total amount of oocysts administered are usually not considered to be sufficient to induce immunity because, in practical situations, the precise amount of coccidia given is difficult to determine. If in such a situation a slight overdose of coccidiostatics is given, this could easily kill the remaining 1% of coccidia, and consequently, no vaccination takes place. Moreover, if the tolerance is below 1%, large amounts of coccidia have to be administered to make up for the loss of coccidia that do not survive the coccidiostatic treatment. This is an impractical situation, if only because growing such large amounts of coccidia is expensive and time-consuming.

A standard amount of coccidiostatic drugs is considered to be an amount that is commonly used in veterinary practice to suppress coccidiosis. Such amounts are indicated in the instructions leaflet of the supplier. For example: amounts of, e.g., between 60 and 125 ppm of monensin or between 40 and 80 ppm of salinomycin are standard amounts of ionophoric coccidiostatic drugs frequently used in veterinary practice.

Ionophoric coccidiostatic drugs belong to the group involved in destruction of membrane integrity. They are very commonly used in the poultry industry. Therefore, a preferred form of this embodiment relates to *Eimeria* strains according to the invention that are tolerant for an ionophoric coccidiostatic drug.

From the group of ionophoric coccidiostatic drugs, monensin and salinomycin are very commonly used. Therefore, a more preferred form of this embodiment relates to *Eimeria* strains according to the invention that are tolerant for the ionophoric coccidiostatic drug monensin or salinomycin.

The group of coccidiostatic drugs that is involved in inhibition of DNA synthesis as mentioned above, more specifically the members of this group toltrazuril and diclazuril, is very suitable for eradicating the coccidia according to the present invention, when desired. Therefore, in a preferred form, the strains according to the invention are sensitive against coccidiostatic drugs involved in inhibition of DNA synthesis. In a more preferred form, the coccidiostatic drug of the azuril group is toltrazuril, letrazuril, or diclazuril.

A typical *E. acervulina* according to the invention has been deposited with the European Collection of Cell Cultures (ECACC), Centre for Applied Microbiology and Research, Salisbury, Wiltshire SP4 0JG, United Kingdom, under deposit number ACA-99112612. A typical *E. tenella* has been deposited at the ECACC under deposit number ACT-99112611, and a typical *E. maxima* strain has been deposited at the ECACC under deposit numbers ACVM-99112610.

A typical *E. acervulina* according to the invention has been deposited with the European Collection of Cell Cultures (ECACC), Centre for Applied Microbiology and Research, Salisbury, Wiltshire SP4 0JG, United Kingdom, under deposit number ACA-99112612. A typical *E. tenella* has been deposited at the ECACC under deposit number ACT-99112611, and two typical *E. maxima* strains have been deposited at the ECACC under deposit numbers ACVM-99112610 and ACM-99112613.

The two *E. maxima* strains are typical for two related, although immunologically slightly different, sub-types within the genus *E. maxima*.

Figure 1:
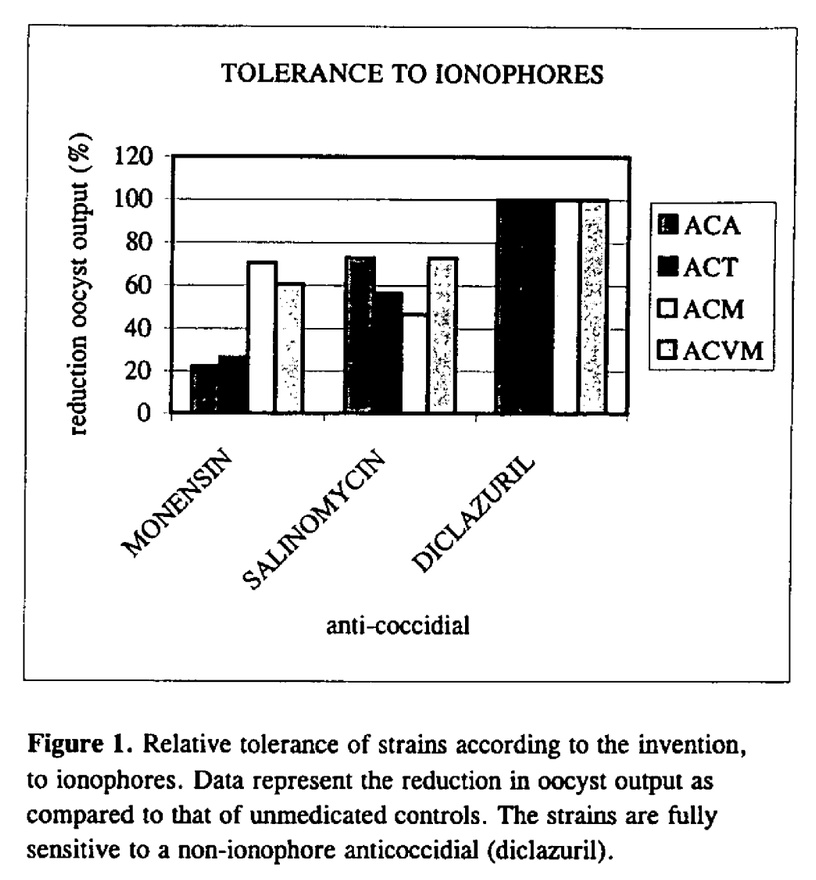
FIG. 1. Important characteristics of the strains according to the invention.

These four strains are tolerant for 110 ppm of monensin and for 60 ppm of salinomycin, sensitive for 1 ppm of diclazuril (see FIG. 1) and the proliferative capacity of the four strains is decreased to 76000 (see Table 1b).

Table 1 shows the low proliferative capacity of the vaccine strains according to the invention.

The proliferative capacity of a single dose of vaccine according to the invention in threeweek-old SPF chickens is approximately 76000 (meaning that 700 sporulated oocysts that are present in a single dose of vaccine yield 53 million oocysts). This level of proliferative capacity is far below that of wild-type strains, as follows from a comparison of Tables $1^a$ and $1^b$.

TABLE 1a typical average proliferative capacity of Eimeria wild type strains (as described in Coccidiosis of man and domestic animals. ISBN 0-8493-6269-5, Eds. Peter L. Long. Shirley, M. W. and Long, P. L. pp 321–229: Control of coccidiosis in chickens: immunization with live vaccines (1990)).

| SPECIES | O.N. | O.Y. | P.C. |
| --- | --- | --- | --- |
| E. acervulina | 100 | 114 × 10⁶ | 1144000 |
| E. tenella | 20 | 50.3 × 10⁶ | 2515000 |
| E. maxima | 50 | 11.5 × 10⁶ | 230000 |
| E. maxima mf | 50 | 13.2 × 10⁶ | 264000 |

(O.N.: oocyst number. O.Y.: oocyst yield. P.C.: proliferative capacity).

TABLE 1b proliferative capacity of a mixture of Eimeria strains according to the invention. A total of 700 oocysts was given, and the total amount of oocysts was determined, in which number all species were represented.

| SPECIES | O.N. | O.Y. | P.C. |
| --- | --- | --- | --- |
| E. acervulina ACA | 500 | | |
| E. tenella ACT | 100 | 53.7 × 10⁶ | 76714 |
| E. maxima ACM | 50 | | |
| E. maxima ACVM | 50 | | |

(O.N.: oocyst number. O.Y.: oocyst yield. P.C.: proliferative capacity).

Another embodiment of the invention relates to microbiological cultures comprising one or more of the *Eimeria* strains according to the invention.

Still another embodiment of the invention relates to vaccines for the protection of animals against coccidiosis that comprise an *Eimeria* strain according to the invention. Strains according to the invention are directly suitable as a basis for a vaccine. Such a vaccine in its simplest form comprises at least one of the *Eimeria* strains according to the invention and a pharmaceutically acceptable carrier. In its easiest form, such a carrier can be water. Also, it can be a buffer solution. Additionally, viscous materials or color markers can be added as described below.

Vaccines according to the invention can be administered to chickens from one day of age. When administering vaccines according to the invention to chickens between one and five days of age, spray-vaccination is recommended for practical reasons. From 4 days of age, vaccination through drinking water is more suitable.

When the vaccine is administered through spraying, small amounts of, e.g., 10-100 mg/ml PVP can be advantageously added to make the spray-suspension slightly viscous.

When adding the vaccine to drinking water or the spray material, Chlorophyll can be advantageously added as a color marker, to check later on if vaccine has indeed been added to the water or spray material.

Vaccination using vaccines according to the invention can be combined from the day of vaccination, e.g., day 1 on with anticoccidial therapy, using the anticoccidial drug for which the tolerant strains according to the invention have been selected.

It is convenient to add more than one *Eimeria* strain according to the invention to the vaccine because it is then possible to vaccinate, in one vaccination step, against more than one *Eimeria* species. *E. acervulina* and *E. tenella* strains according to the invention would be the basis of such a combination vaccine. Especially since it was noticed that antigenically different forms of *E. maxima* exist, it is convenient to additionally incorporate two *E. maxima* strains according to the invention in one combination vaccine. Such a vaccine efficiently protects against *E. tenella, E. acervulina*, and several antigenically different *E. maxima* variants. Therefore, in a preferred form, the vaccine according to the invention comprises a combination of *Eimeria* strains according to the invention.

In addition to one or more of the strains according to the invention, the vaccine may advantageously comprise antigenic material of at least one other microorganism or virus. Such a pathogenic microorganism may, e.g., be another parasite. It can also be of bacterial or viral origin. Usually, the antigenic material will be derived from a virus or microorganism pathogenic to poultry. The antigenic material can be, e.g., a live attenuated form of the virus or the microorganism. It can also be an inactivated form thereof. Also, antigenic subunits of the whole organism can be used as the antigenic material.

A vaccine that comprises such an additional pathogen or antigenic material thereof has the advantage that it induces protection against several infections at the same time. Therefore, in a more preferred form of this embodiment, the vaccine further comprises at least antigenic material of one other virus or microorganism pathogenic to poultry.

In an even more preferred form, the microorganism or virus is selected from the group consisting of *Eimeria*, Infectious Bronchitis virus, Newcastle Disease virus, Infectious Bursal Disease (Gumboro), Chicken *Anemia* agent, Avian Reovirus, *Mycoplasma gallisepticum*, Turkey Rhinotracheitis virus, *Haemophilus paragallinarum* (Coryza), Chicken Poxvirus, Avian Encephalomyelitisvirus, Fowl Cholera and *E. coli*.

Still another embodiment of this invention relates to the use of an *Eimeria* strain according to the invention for the preparation of a vaccine for the prevention of coccidiosis.

Another embodiment of the invention relates to methods for the preparation of a vaccine according to the invention. Such methods in a simple form comprise the admixing of a coccidiosis strain according to the invention and a pharmaceutically acceptable carrier.

EXAMPLE 1

Experimental Set-Up

An experiment was conducted to assess the safety and efficacy of spray-vaccination of broilers against coccidiosis using different doses of the strains according to the invention. The vaccine was administered to the birds by spraying at one day of age. The take of the vaccine was determined by analysis of oocyst shedding in fecal samples taken from individual animals six days after vaccination. Gut lesion scores were determined weekly to assess the safety of the vaccine. The development of immunity against coccidiosis was determined by experimental challenge infection at four weeks after vaccination. In addition, growth and feed conversion rates were determined for all individual floor pens.

TABLE 2

Specification of the composition of the vaccine. The strains mentioned are the strains as deposited. The numbers refer to the absolute number of sporulated oocysts in a single dose of the five-fold dose group.

Vaccine

| SPECIES | STRAIN | NUMBER OOCYSTS |
| --- | --- | --- |
| *E. acervulina* | ACA | 2500 |
| E. tenella | ACT | 500 |
| E. maxima | ACM | 250 |
| E. maxima | ACVM | 250 |

TABLE 3

Composition of carrier solution of the vaccine.

| COMPOUND | SUPPLIER | CONCENTRATION |
| --- | --- | --- |
| NaH2PO4.2H2O | Merck | 7.48 mg/ml |
| Na2HPO4.2H2O | Merck | 4.38 mg/ml |
| NaCl | Merck | 3.7 mg/ml |
| PVP (Kollidon 90F) | BASF | 50 mg/ml |
| Chlorophyll Cu—Na-complex (E141) | William Ransom | 1 mg/ml |
| Distilled water | | ad 1 liter |

PVP = polyvinylpyrrolidone;

Preparation of Inoculate

The vaccines (different doses per ml) were prepared by diluting the strains according to the invention with carrier solution to the required titer. Six preparations were made:

Five-fold dose (the vaccine);

Two-fold dose (prepared from vaccine by dilution with carrier solution);

Single dose (prepared from vaccine by dilution with carrier solution);

Half-a-dose (prepared from vaccine by dilution with carrier solution);

One-fifth-a-dose (prepared from vaccine by dilution with carrier solution); and

Control (carrier solution only).

Vaccination/Challenge

The vaccine was administered by spraying (0.5 ml/animal). All animals that received a particular dose of the vaccine were sprayed in a single action, starting with the control group followed by the one-fifth dose group, and so on.

All animals received feed containing 100 ppm ionophore (monensin) until 37 days of age, except for the animals that received a coccidiosis challenge infection at 28 days of age. These animals received feed with ionophore until 21 days of age and feed without ionophore from day 21 on.

Animals

One-day old female broiler chickens (Ross, obtained from Cobroed, Lievelde, The Netherlands) were used in the experiment. Animals were exempt from vaccination against Newcastle Disease Virus.

Challenge Strains

Heterologous *Eimeria* parasites were originally obtained from the Central Veterinary Laboratory (Weybridge, U.K.; *E. tenella* and *E. acervulina*), and Houghton Poultry Research Station (Houghton, U.K.; *E. maxima*).

TABLE 4

Specifications of the challenge inoculum. The dose refers to the number of sporulated oocysts contained in a single dose of challenge material administered per chicken in a volume of 1 ml.

| SPECIES | DOSE |
| --- | --- |
| *E. acervulina* | $12 \times 10^4$ |
| *E. tenella* | $12 \times 10^3$ |
| *E. maxima* | $14 \times 10^3$ |

Treatment Schedule

The groups of animals were treated as follows:

760 animals received ⅕ vaccine doses, of which 180 were challenged;

760 animals received ½ vaccine doses, of which 180 were challenged;

760 animals received 1 vaccine doses, of which 180 were challenged;

760 animals received ²⁄₁ vaccine doses, of which 180 were challenged;

760 animals received ⁵⁄₁ vaccine doses, of which 180 were challenged; and 760 animals were kept as control, of which 180 were challenged.

Determination of Body Weight

The body weight of the animals was determined at two-weekly intervals, starting at day 1 of age. Body weight was determined by group weighing, except at 28 days of age, when the animals of the floor pens marked 'CHALLENGE' were weighed individually, and at the end of the experiment when all animals were weighed individually.

Cloaca Samples

At day 7 of the experiment, ten animals were selected from each floor pen as they came to hand. Of these animals, feces samples were taken from the cloaca. These samples were checked for the presence of oocysts. For each dose of vaccine administered, 80 animals were evaluated.

Determination of Lesions of the Gut Epithelium

The degree of macroscopic pathology of the gut epithelium was assessed by determination of the lesion score, according to the procedure of Johnson and Reid (Johnson, J and Reid, W M, *Experimental Parasitology* 28, 30-36 (1970)). At day 7, 14, 21, and 28 of the experiment, five wing-tagged animals were selected from each floor pen as they came to hand and sacrificed for determination of lesion score. For each dose of vaccine, 40 animals were evaluated per time point.

Oocyst Shedding

Twice a week, approximately 15 fresh droppings were collected from each individual floor pen. Droppings from each floor pen were pooled. The number of oocysts per gram of feces was determined according to routine procedures. Thus, for each dose of vaccine, 8 samples were evaluated per time point.

Feed Conversion

The amounts of feed administered (and the amounts of residual feed) were determined at days 1, 14, 21, 28, 37, and 42. Taking into account the actual number of chickens in the floor pens during the specific time periods, the feed conversion was calculated.

Challenge Infection

Animals were selected as they came to hand and were orally inoculated with a mixture of sporulated oocysts of *E. acervulina*, *E. tenella*, and *E. maxima* in a volume of 1 ml as specified in Table 4.

Results

Efficiency of Oocyst Administration by Spraying

It appeared that on average, 81% of the oocysts could be recovered in the samples.

TABLE 5

Recovery of oocysts in samples taken during the act of spraying expressed as a percentage of the theoretical value.

| INOCULUM | % OOCYSTS RECOVERED |
|---|---|
| ⅕ DOSE | 103 |
| ½ DOSE | 65 |
| SINGLE DOSE | 97 |
| DOUBLE DOSE | 62 |
| FIVE-FOLD DOSE | 78 |
| MEAN | 81.0 ± 18.5% |

Take of Vaccine

Eighty (80) animals were evaluated per vaccine-dose group. At the recommended dose level (one single dose), in 95% of the chickens, oocysts were detected in fecal samples from the cloaca six days after vaccination, which is indicative for ingestion of vaccine (Table 6). Doubling the recommended dose level increased vaccine take to 100%. When one-fifth the recommended dose was used, 70% of the animals still excreted oocysts. Nonvaccinated control animals shed no oocysts six days after treatment.

TABLE 6

Recovery of oocysts in feces samples taken from the cloaca of chickens, six days after administration of the vaccine. Data are expressed as the percentage of chickens that had positive samples.

| INOCULUM | % POSITIVE ANIMALS |
|---|---|
| CONTROL | 0.0 |
| ⅕ DOSE | 70.0 |
| ½ DOSE | 81.3 |
| SINGLE DOSE | 94.9 |
| DOUBLE DOSE | 100 |
| FIVE-FOLD DOSE | 100 |

Spreading of Vaccine

Figure 2:
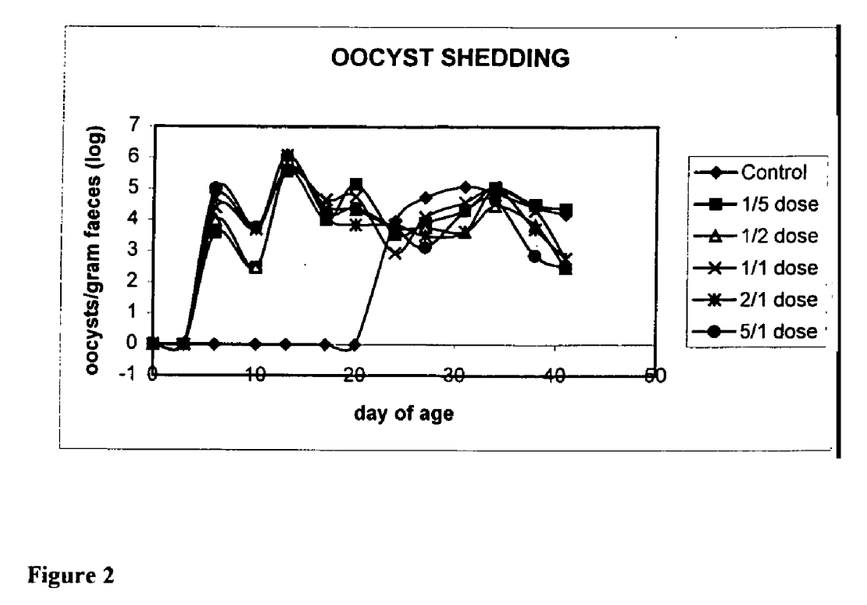
FIG. 2. Mean oocyst output by chickens of replicate floor pens that received different doses of vaccine at day one of age and a challenge infection at day 28 of age. Data are represented as the logarithmic value of the number of oocysts per gram feces (mean of 8 floor pens before challenge, mean of two floor pens after challenge).

Oocysts derived from the vaccine strains were detectable in the litter one week after vaccination, and spread among each flock (FIG. 2). There was a positive dose-effect relationship between the dose of vaccine administered and the oocyst output after vaccination: the more coccidia were given in the vaccine, the more coccidia were shedded. At 13 days after vaccination, there was a peak of oocyst output in all vaccinated groups: no oocysts were detected in feces of the nonvaccinated control animals until day 13, when two out of eight floor pens were slightly positive.

Figure 3:
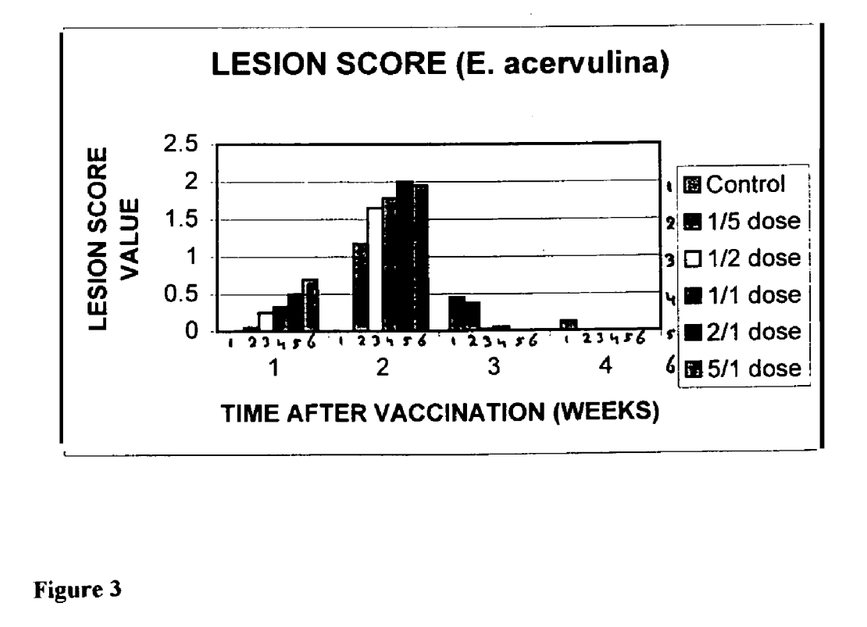
FIG. 3. The development of lesion scores due to *E. acervulina* during the pre-challenge period in representative samples (n=40) of chickens taken from floor pens that received the same vaccine dose (5 chickens of each floor pen, 8 replicates).

Safety of the Vaccine a) Lesion Score:

Per vaccine-dose group, 40 animals were evaluated for determining lesions in the gut. Lesions were mild and of a transient nature (FIG. 3). They were first detected at 6 days after vaccination with a peak one week later, after which time they declined to undetectable levels (27 days after vaccination). There was a positive dose-effect relationship between the dose applied and the lesion score value. At the recommended dose level, the mean lesion score was 1.8 (±0.5) at the peak of lesion development. Even when five times the recommended dose was administered, the mean lesion score was only 2.0 (±0.6). Lesions were mainly due to the development of E. acervulina oocysts. Occasionally, mild lesions due to E. tenella and E. maxima development were found in vaccinated animals at 20 days after vaccination.

b) Performance in the Absence of Experimental Challenge

The vaccine had a slight transient effect on the performance of the animals until 28 days of age (feed conversion, Table 7), after which period of time this slight reduction was completely restored. At 42 days of age, the feed conversion rate was equal in all experimental groups (excluding the groups that were challenged at day 28), irrespective of the dose used for vaccination. It thus appeared that vaccination with vaccine according to the invention did not affect the performance of broiler chickens.

TABLE 7

Effect of administration of different doses of the vaccine at day 1 of age on the feed conversion of broiler chickens at 14, 28 and 42 days of age.

| | FEED CONVERSION | | |
|---|---|---|---|
| INOCULUM | 14 DAYS | 28 DAYS | 42 DAYS |
| CONTROL | 1.058 | 1.362 | 1.670 |
| ⅕ DOSE | 1.064 | 1.396 | 1.666 |
| ½ DOSE | 1.070 | 1.398 | 1.662 |
| SINGLE DOSE | 1.069 | 1.409 | 1.676 |
| DOUBLE DOSE | 1.077 | 1.406 | 1.666 |
| FIVE-FOLD DOSE | 1.092 | 1.411 | 1.669 |

Efficacy of the Vaccine

Two weeks after the challenge infection, the mean body weight and feed conversion rate of all vaccinated groups of animals were better than that of control groups (Table 8).

TABLE 8

Effect of administration of different doses of the vaccine at day 1 of age on the mean body weight and feed conversion of broiler chickens (determined at 42 days of age; n = 150) that were challenged two weeks earlier with Eimeria parasites.

| INOCULUM | BODY WEIGHT (g) | FEED CONVERSION |
|---|---|---|
| CONTROL | 2093 | 1.694 |
| ⅕ DOSE | 2172 | 1.661 |
| ½ DOSE | 2205 | 1.647 |
| SINGLE DOSE | 2233 | 1.651 |
| DOUBLE DOSE | 2137 | 1.655 |
| FIVE-FOLD DOSE | 2187 | 1.642 |

Feed conversion is the amount of feed (kg) that is needed for 1 kg of chicken meat. Feed conversion is often expressed in points: one point is 10 g. The feed conversion rate of groups of animals that received the five-fold dose, single dose, and half-dose of vaccine were statistically significantly better than that of the control groups. The mean body weight of the animals that were vaccinated with the recommended dose was 140 grams higher than that of control animals (2233 grams and 2093 grams, respectively). The feed conversion rate of the animals that were vaccinated with the recommended dose was 4.3 points better than that of control animals (1.651 and 1.694, respectively).

In conclusion, broilers that are reared in floor pen conditions can be protected against coccidiosis by spray-vaccination with the vaccine according to the invention at one day of age. The vaccine has a limited transient effect on the performance of the animals during the first three weeks of the rearing period, which is compensated for completely during the remainder of the rearing period. When vaccinated animals are challenged, they appear to be protected against the negative effects of coccidiosis.

The invention claimed is:

1. A coccidiosis vaccine comprising a pharmaceutically acceptable carrier; and oocysts from at least one strain of Eimeria coccidia having:

a tolerance for at least one ionophoric drug, a sensitivity to at least one DNA synthesis inhibitor drug, and a decreased proliferative capacity, and wherein the at least one strain Eimeria coccidia is selected from the group consisting of Eimeria acervulina strain ACA-99112612, *Eimeria tenella* strain ACT-99112611, and *Eimeria maxima* strain ACVM-99112610.

2. The coccidiosis vaccine according to claim 1, further comprising antigenic material of at least one virus or other microorganism pathogenic to poultry.

3. The coccidiosis vaccine according to claim 2, wherein said at least one virus or other microorganism is selected from the group consisting of *Eimeria tenella, E. necatrix, E. maxima, E. brunette, E. acervulina, E. mitis* and *E. praecox*, Infectious Bronchitis virus, Newcastle Disease virus, Infectious Bursal Disease, Chicken Anemia agent, Avian Reovirus, *Mycoplasma gallisepticum*, Turkey Rhinotracheitis virus, *Hemophilus paragallinarum*, Chicken Poxvirus, Avian Encephalomyelitisvirus, Fowl Cholera and *E. coli*.

4. A coccidiosis vaccine, comprising: a pharmaceutically acceptable carrier; and oocysts from at least two strains of *Eimeria* coccidia, said at least two strains of *Eimeria* coccidia being selected from the group consisting *Eimeria acervulina* strain ACA-99112612, *Eimeria tenella* strain ACT-99112611, and *Eimeria maxima* strain ACVM-99112610.

* * * * *

UNITED STATES PATENT AND TRADEMARK OFFICE
CERTIFICATE OF CORRECTION

| | |
|---|---|
| PATENT NO. | : 7,247,309 B2 |
| APPLICATION NO. | : 09/739561 |
| DATED | : July 24, 2007 |
| INVENTOR(S) | : Arnoldus Nicolaas Vermeulen et al. |

Page 1 of 1

It is certified that error appears in the above-identified patent and that said Letters Patent is hereby corrected as shown below:

Title Page,
In ITEM (56) References Cited:
FOREIGN PATENT DOCUMENTS
Page 1, 1ˢᵗ column, 1ˢᵗ entry,     delete "EP   0-047662   *   2/1982"

In the claims:
CLAIM 3,   COLUMN 13,   LINE 9,    change "*E. brunette*," to --*E. brunetti*,--
CLAIM 4,   COLUMN 14,   LINE 6,    change "group consisting" to --group consisting of--

Signed and Sealed this
Thirtieth Day of August, 2011

David J. Kappos
*Director of the United States Patent and Trademark Office*